(12) United States Patent
Schoonenberg et al.

(10) Patent No.: US 9,757,076 B2
(45) Date of Patent: Sep. 12, 2017

(54) COMBINING X-RAY WITH INTRAVASCULARLY ACQUIRED DATA

(75) Inventors: Gert Anonius Franciscus Schoonenberg, Eindhoven (NL); Nicolaas Hytke Bakker, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1549 days.

(21) Appl. No.: 12/515,028

(22) PCT Filed: Nov. 19, 2007

(86) PCT No.: PCT/IB2007/054688
§ 371 (c)(1),
(2), (4) Date: Dec. 3, 2009

(87) PCT Pub. No.: WO2008/062358
PCT Pub. Date: May 29, 2008

(65) Prior Publication Data
US 2010/0094124 A1    Apr. 15, 2010

(30) Foreign Application Priority Data
Nov. 22, 2006    (EP) .................................... 06124558

(51) Int. Cl.
*A61B 6/12*    (2006.01)
*A61B 5/00*    (2006.01)
(Continued)

(52) U.S. Cl.
CPC .............. *A61B 6/12* (2013.01); *A61B 5/0084* (2013.01); *A61B 6/481* (2013.01); *A61B 6/504* (2013.01);
(Continued)

(58) Field of Classification Search
CPC ......... A61B 5/0084; A61B 6/12; A61B 6/481; A61B 6/504; A61B 6/5247
See application file for complete search history.

(56) References Cited

U.S. PATENT DOCUMENTS 5,771,895 A    6/1998  Slager
6,175,757 B1 *  1/2001  Watkins et al. ............... 600/425
(Continued)

FOREIGN PATENT DOCUMENTS

| JP | H10137238 A | 5/1998 |
|---|---|---|
| WO | 0130254 A1 | 5/2001 |
| WO | 2005024729 A1 | 3/2005 |

OTHER PUBLICATIONS

Lindeberg, T.: "Feature Detection With Automatic Scale Selection"; International Journal of Computer Vision, vol. 30 (2), pp. 79-116.
(Continued)

*Primary Examiner* — Joseph M Santos Rodriguez (57) ABSTRACT

A system for estimating a position in an x-ray projection image that corresponds to a projected probe position of an intravascular probe at a time of intravascular ultrasound (IVUS) imaging. A marker detector identifies in the x-ray projection image a plurality of projected positions of markers that are located at predetermined distances along an acquisition trajectory of the intravascular probe. The projected positions are interpolated to obtain the projected probe position on the trajectory. The projected probe position corresponds to a location of the intravascular probe at a time of the IVUS imaging and is based on a distance along the acquisition trajectory between the intravascular probe at the time of the IVUS imaging and at least one of the markers.

12 Claims, 3 Drawing Sheets

(51) Int. Cl.
*A61B 6/00* (2006.01)
*A61B 8/12* (2006.01)
*A61B 8/08* (2006.01)
*G06T 7/33* (2017.01)
*G06T 7/38* (2017.01)
*A61B 8/00* (2006.01)
*A61B 6/02* (2006.01)

(52) U.S. Cl.
CPC .............. *A61B 6/5247* (2013.01); *A61B 8/12* (2013.01); *A61B 8/5238* (2013.01); *G06T 7/33* (2017.01); *G06T 7/38* (2017.01); *A61B 5/7285* (2013.01); *A61B 6/027* (2013.01); *A61B 6/541* (2013.01); *A61B 8/543* (2013.01); *G06T 2207/10116* (2013.01); *G06T 2207/10132* (2013.01); *G06T 2207/30101* (2013.01); *G06T 2207/30204* (2013.01)

(56) References Cited

U.S. PATENT DOCUMENTS

| | | | |
|---|---|---|---|
| 6,351,513 B1 * | 2/2002 | Bani-Hashemi et al. | ........ 378/8 |
| 6,370,421 B1 | 4/2002 | Williams et al. | |
| 9,393,079 B2 | 7/2016 | Weese et al. | |
| 2006/0036167 A1 | 2/2006 | Shina | |
| 2006/0064006 A1 | 3/2006 | Strommer et al. | |
| 2010/0094124 A1 | 4/2010 | Schoonenberg et al. | |

OTHER PUBLICATIONS

Egmont-Petersen et al: "Recognition of Radiopaque Markers in X-Ray Images Using a Neural Network as Nonlinear Filter"; Pattern Recogniton Letters, vol. 20, pp. 521-533.

* cited by examiner

COMBINING X-RAY WITH INTRAVASCULARLY ACQUIRED DATA

FIELD OF THE INVENTION

The invention relates to combining an x-ray image with intravascularly acquired data. More particularly, the invention relates to a system for estimating a position in an x-ray projection image corresponding to a projected probe position of an intravascular probe at a time of acquiring data from the intravascular probe.

BACKGROUND OF THE INVENTION

In catheter examinations of the heart, a number of angiographic x-ray images of the heart are usually generated from various directions, a contrast agent typically being injected during the recording. The angiograms of the vascular system that are thus obtained may be of assistance, for example, in locating the site of a lesion that is to be treated, or else they may be used as (static) road maps for navigating a catheter during a subsequent medical intervention.

Moreover, so-called intravascular ultrasound probes (IVUS probes) are used, which can be guided for example by means of a catheter through a vessel and generate ultrasound section images transversely to the vessel axis. Ultrasound images are often generated in a so-called pullback sequence using an IVUS probe. In this case, the IVUS probe is pulled back through the vessel at a defined speed while at the same time recording a series of ultrasound images. The IVUS images provide useful additional information about the vessel or a vessel lesion, for example the length of a vessel section affected by a disease, the minimum/maximum thickness of a vessel, the type of a deposit and the like. WO 2005/024729 discloses a device, used to display a vessel or a section of a vascular system, comprising the following components:
a) a (data) memory in which a sequence of intravascular ultrasound images is stored, the ultrasound images being indexed by the respective locations (x) of their recording in the vessel. Said ultrasound images may have been generated, for example, with the aid of an intravascular ultrasound probe. In particular, the images may come from an IVUS pullback sequence, wherein as the IVUS probe is being pulled back, the respective stopping location of the IVUS probe in the vessel is determined in parallel by means of further imaging. The latter may moreover be estimated from existing images of the vascular system (angiographs).
b) a data input for information which describes (at least) a current location in the vessel. By way of example, a pointer (mouse, etc.) could be connected to this input, by means of which pointer a user indicates, on a road map, a current location of interest to him in the vessel, or else a locating device could be connected to said input, which locating device detects, for example by means of magnetic fields, the current stopping location of an intervention device on a catheter.
c) a display unit, such as a monitor, for displaying images of the vessel.

The device disclosed in WO 2005/024729 comprising the described components is furthermore designed to select from said memory at least one ultrasound image and to display it on the display unit, wherein the ultrasound image corresponds to the current location in the vessel indicated at the data input. By way of example, an ultrasound image whose associated recording location is identical to the current location or is no more than a predefined distance from the latter may be selected from the memory. The selection function may be implemented in the device for example by means of a suitably programmed microprocessor.

SUMMARY OF THE INVENTION

It would be advantageous to have an improved way of combining an x-ray image with intravascularly acquired data. To better address this concern, in a first aspect of the invention a system is presented, that comprises:
- a marker detector for identifying in the x-ray projection image a plurality of projected positions of markers, the markers being located at predetermined distances along an acquisition trajectory of the intravascular probe; and
- an interpolator for interpolating the projected positions to obtain the projected probe position on the acquisition trajectory, the projected probe position corresponding to a location of the intravascular probe at a time of acquiring the data, in dependence on a distance along the acquisition trajectory between the intravascular probe at the time of acquiring the data and at least one of the markers.

The system can efficiently provide the projected position of the probe. The interpolator makes it unnecessary to create a 3D representation of the acquisition trajectory and/or of the probe position. The probe can be localized in the projection image without the need to acquire images taken from multiple directions.

The system provides information regarding to which position on the x-ray image the data corresponds, i.e., where in the body the data were acquired. This information is useful in many ways. For example, it facilitates displaying the data in relation to the x-ray image, and it facilitates treatment planning. A three-dimensional reconstruction of the vessel or three-dimensional positioning equipment is not required. The probe may be localized in the x-ray image that shows the marker positions.

The markers and the probe may be mounted on a single catheter. Alternatively, the markers and the probe are mounted on one or more catheters and/or (guide)wires. For example the distance between the successive markers on the catheter/wire is known. The markers may be small radiopaque objects for easy and automatic detection in the x-ray image.

The detected markers may be transformed into a trajectory. The markers on a single x-ray image do not necessarily provide enough information to establish the trajectory in 3D; however, it does provide sufficient information to establish the trajectory followed by the probe as seen on the x-ray image. This means, that it is possible to map each point on the trajectory to a corresponding point on the x-ray image, even without knowing the exact three-dimensional trajectory.

The markers and their known relative positions along the trajectory allow the mapping of data acquired with the probe to locations on the x-ray image to be relatively accurate and robust, while allowing the acquisition procedure and the viewing of images to be relatively efficient and user friendly.

An embodiment comprises an indicator for indicating in an angiographic projection image the projected probe position, wherein the angiographic projection image and the x-ray projection image have a same acquisition orientation with respect to a patient.

An x-ray angiographic image may be acquired in addition to the x-ray image providing a view of the markers. Both x-ray images are acquired from the same perspective or at least in such a way that the positions in the two angiograms can be spatially related to each other. This is for example the case if the two images were acquired from the same orientation, but with a different magnification. In this case, since the position is known in the x-ray image showing the markers, it can be converted to a position in the angiogram. The view of the markers and the view of the vessels may also be combined in a single x-ray image.

In an embodiment, the interpolator is arranged for interpolating the projected positions of the markers along a projected vessel visible in an angiographic projection image, wherein the angiographic projection image and the x-ray projection image have a same acquisition orientation with respect to a patient.

The projected vessel may be used to more accurately determine the acquisition trajectory in between the markers.

An embodiment comprises means for establishing the distance along the acquisition trajectory between the intravascular probe and at least one of the markers in dependence on a reference probe position and a distance along the acquisition trajectory traversed by the probe in between the reference probe position and the location of the intravascular probe at the time of acquiring the data.

This is an efficient way to establish the distance along the acquisition trajectory between the intravascular probe and at least one of the markers. For example the reference distance value corresponds to a starting or an end point of the acquisition trajectory. Because of the predetermined relative distances of the markers along the trajectory, it is possible to associate a distance traversed along the trajectory with a position along the trajectory between two successive markers.

In an embodiment, the reference probe position is a probe starting position, the acquisition trajectory is a probe pullback trajectory, and the distance along the acquisition trajectory traversed by the probe is a length of the probe pullback trajectory from the probe starting position to the position of the probe at the time of acquiring the data. Pullback is an efficient acquisition scheme, and is compatible with the system set forth. An embodiment comprises means for determining the length of the probe pullback trajectory from the probe starting position to the position of the probe at the time of acquiring the data in dependence on a pullback speed and a pullback duration.

This is convenient in the case of automatic pullback.

In an embodiment, the intravascular probe is an intravascular ultrasound probe. Intravascular ultrasound (IVUS) probes are commonly used to assess lesion severity and lesion extent. This embodiment combines x-ray and IVUS.

An embodiment comprises a probe detector for identifying the probe in the x-ray image; wherein the interpolator is operative also in dependence on a position of the probe in the x-ray image and a distance traveled by the probe in between the position of the probe in the x-ray image and the position of the probe at the time of acquiring the data.

The identified probe may be used as a probe reference location.

An embodiment comprises:
a user input for enabling a user to select the data for viewing;
a display for displaying the selected data and the angiographic projection image; and
an indicator for indicating in the angiographic projection image the position of the probe at the time of acquiring the data.

This is a convenient and user-friendly way of visualizing the located point in the image. Data may be collected and localized for many different locations, and the user input may allow any of the data to be selected.

In an embodiment, the indicator is arranged for also indicating in the x-ray image an orientation of the probe at the time of acquiring the data in dependence on a direction of the acquisition trajectory at the position of the probe at the time of acquiring the data.

Showing the orientation of the probe further helps in interpreting the data. As the interpolated trajectory is available and the orientation of the probe follows the trajectory, it can be used to determine the orientation of the probe.

As a second aspect of the invention there is provided an x-ray imaging apparatus for estimating a position in an x-ray projection image corresponding to a projected probe position of an intravascular probe at a time of acquiring data from the intravascular probe, which apparatus comprises:
an x-ray generator and an x-ray detector for obtaining the x-ray projection image;
an input for receiving the data acquired from the intravascular probe;
a marker detector for identifying in the x-ray projection image a plurality of projected positions of markers, the markers being located at predetermined distances along an acquisition trajectory of the intravascular probe; and
an interpolator for interpolating the projected positions to obtain the projected probe position on the acquisition trajectory, the projected probe position corresponding to a location of the intravascular probe at a time of acquiring the data, in dependence on a distance along the acquisition trajectory between the intravascular probe at the time of acquiring the data and at least one of the markers.

This embodiment facilitates full integration of x-ray and IVUS in the catheterization lab.

As a third aspect of the invention there is provided a method of estimating a position in an x-ray projection image corresponding to a projected probe position of an intravascular probe at a time of acquiring data from the intravascular probe, which method comprises:
identifying in the x-ray projection image a plurality of projected positions of markers, the markers being located at predetermined distances along an acquisition trajectory of the intravascular probe; and
interpolating the projected positions to obtain the projected probe position on the acquisition trajectory, the projected probe position corresponding to a location of the intravascular probe at a time of acquiring the data, in dependence on a distance along the acquisition trajectory between the intravascular probe at the time of acquiring the data and at least one of the markers.

BRIEF DESCRIPTION OF THE DRAWINGS

These and other aspects of the invention will be further elucidated and described with reference to the drawing, in which.

DETAILED DESCRIPTION OF EMBODIMENTS

Figure 1:
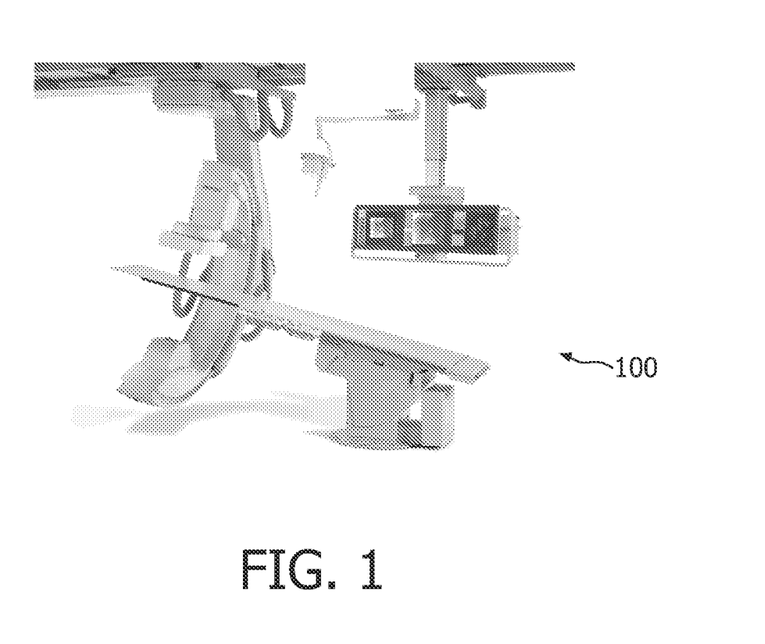
FIG. 1 shows an example x-ray system used in catheterization procedures.

FIG. 1 illustrates an x-ray imaging system 100 used during cardiovascular interventions such as catheterization procedures. During cardiovascular interventions, in addition to x-ray imaging, intravascular ultrasound (IVUS) imaging can be used to obtain cross-sectional images of a vessel containing valuable information about the vessel wall. IVUS imaging is typically performed by pullback through a vessel segment, which may be motorized, and may result in thousands of cross-sectional vessel images. Correspondence between the location where a particular IVUS image is taken and the corresponding location in the x-ray image of the vessel (angiogram) is usually not shown directly to the interventionalist. This makes it hard to guide treatment that is based on locations as seen on x-ray. It would be advantageous if the interventional cardiologist could see where a particular IVUS image is taken with respect to the vessel tree visible in an angiogram.

Figure 2:
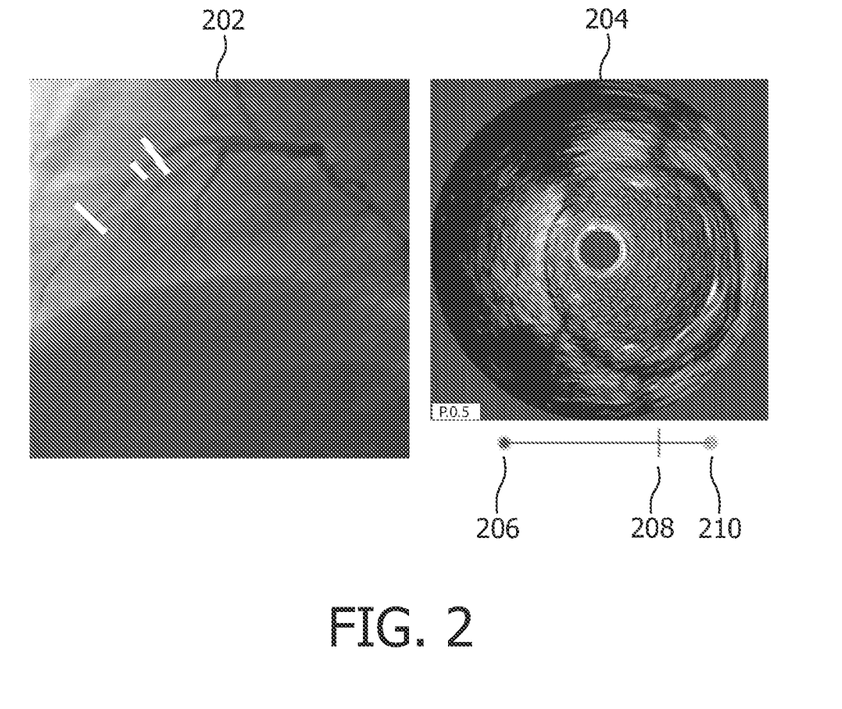
FIG. 2 shows an x-ray angiogram and an IVUS image.

FIG. 2 illustrates an angiogram 202 and an IVUS image 204. In the angiogram 202, three white line markers have been drawn to indicate positions of the IVUS probe. The two longer lines indicate the starting position and end position of the IVUS probe, and the shorter line indicates the position of the probe at the time of acquiring the IVUS image 204. These markers correspond to the time line indicating acquisition start time 206, time 208 of acquiring the image 204, and acquisition end time 210. The shorter line drawn in angiogram 202 thus indicates the position within the vessel to which the IVUS image 204 corresponds.

Figure 3:
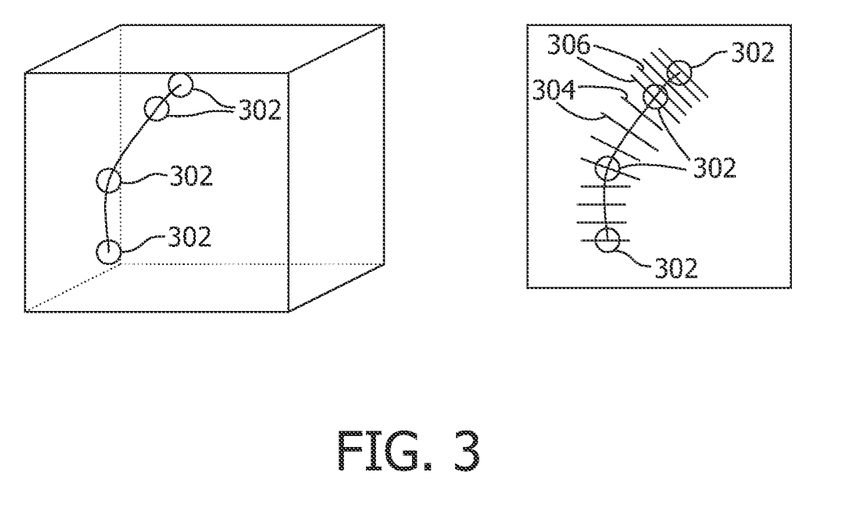
FIG. 3 shows a diagram illustrating positions along a vessel.

FIG. 3 illustrates on the left a 3D visualization of a catheter with markers 302. On the right, the Figure shows a projection image of the same catheter with markers 302. The markers are distributed on the catheter equidistantly. Indicators 304, 306 show the positions along the catheter that correspond to successive IVUS images acquired during a pullback acquisition. Because the pullback is performed with a fixed pullback speed, the distance between successive positions along the catheter in 3D space is identical for each pair of successive images. It can be seen that, due to foreshortening, the distance between the positions in the 2D projection image is not the same for all pairs. For example, the distance between the positions 304 is larger than between positions 306. This illustrates that the markers 302 can be used to determine the positions 304, 306 in the 2D projection image.

Known methods to register IVUS images to x-ray images are based on three-dimensional reconstruction methods to establish the pullback path of the catheter in 3D. To create the three-dimensional reconstruction, a special acquisition is required such as computed tomography (CT) or 3D Rotational Angiography (3D-RA). Alternatively, at least two angiograms from different perspectives are required. All these acquisitions add to the x-ray dose and contrast agent liquids applied to the patient.

3D reconstruction methods work for instance by acquiring a rotational run and reconstructing either the catheter or the vessel. Then in the 3D reconstructed volume the distance can be calculated and mapped back on a static (single shot) image. Also a 3D model can be created by taking two single shot images (ideally 90 degrees apart). Again in the 3D modeled volume distance measures can be made and mapped back. All these methods have in common that first a 3D reconstruction needs to be generated from at least 2 views. Steps to obtain the 3D model are complex and do not fit well into the workflow, especially the workflow of cardiac interventions.

In an embodiment, one or more x-ray images, taken with the same orientation of the x-ray gantry and patient, are used for IVUS registration. 3D reconstruction is not needed. Using an IVUS catheter with multiple markers on it, with known distance between the markers, the foreshortening between all pairs of adjacent markers can be calculated from a single x-ray image. The 2D x-ray image is taken just before pullback so that the markers on the IVUS catheter correspond to locations on the pullback path and the probe as visible on the x-ray image corresponds to a starting position of the pullback. By assuming a constant pullback speed, the position of the probe along the pullback path at the time of acquiring each IVUS frame can be established. From this information, the system can establish the number of markers that have been passed by the probe, and the exact location between two successive markers on the catheter. Having this information, it is possible by interpolation to establish the corresponding point on the trajectory between the two successive markers in the x-ray image. Alternatively, an IVUS catheter without markers can be used and a marker guide-wire can be used that contains markers spaced at known distances. These marker guide-wires are widely available on the market. The guide wire is inserted through the lumen of the IVUS catheter ensuring correspondence of the markers on the guide wire with the pullback path.

By using known automatic marker detection algorithms the application can be fully automated. Such automatic marker detection algorithms are known from "Feature detection with automatic scale selection", by T. Lindeberg, in: International Journal of Computer Vision, 30(2), pp. 79-116, 1998, referred to hereinafter as "Lindeberg"; and from "Recognition of radiopaque markers in x-ray images using a neural network as nonlinear filter", by M. Egmont-Petersen and T. Arts, in: Pattern Recogn. Lett., vol. 20, pp. 521-533, 1999, referred to hereinafter as "Egmont-Petersen". It is possible to improve the detection by taking into account the spatial distribution of detected (candidate) markers and by only considering (candidate) markers in or near one or more vessels visible in the angiogram.

Needing only one x-ray gantry position for registration eliminates the requirement to use a biplane system or the need to acquire two x-ray images from two different positions (ideally 90 degrees apart) or a rotational scan and the subsequent 3D reconstruction. Needing only one or more projection images from a single gantry position influences the workflow of the physician in a positive way. This is even more so because the physician already is used to acquire the angiogram/x-ray image for diagnostic purposes and for treatment planning.

In an embodiment, the x-ray gantry is positioned by a physician and an angiogram is created by injecting contrast agent in a vessel (e.g. artery) of interest and simultaneously acquiring one or more x-ray images. This angiogram is used for diagnostic purposes, but also stored in a digital storage medium for automatic processing. Also, with the x-ray gantry in the same position, one or more x-ray images are acquired while an intravascular probe has been inserted in the vessel of interest and a catheter or wire with one or more markers has also been inserted in the vessel of interest. Advantageously, the markers and the probe are attached to the same intravascular (guide)wire or catheter, but this is not required. Alternatively, only the markers are present in the vessel and the probe is not. The x-ray image thus created contains information about the location of the markers along the wire or catheter, i.e., along the vessel lumen. Advantageously contrast agent is not injected while acquiring the image of the markers, because the contrast agent makes it more difficult to automatically detect the markers. Alternatively the two types of x-ray images (angiogram and x-ray with markers) can be combined in one x-ray image by inserting the markers and/or probe before injecting the contrast agent. However current detection algorithms have some difficulty with detecting the markers in such an image.

Also, a series of IVUS images is acquired while pulling the catheter on which the IVUS probe is mounted with a fixed pullback speed. Because of the fixed pullback speed, it is known for each acquired image how much the catheter has been pulled out of the body; and hence it is known how far the probe has traveled along the pullback trajectory. This information is used to calculate a correlation between the x-ray images and the IVUS images.

An embodiment comprises image processing steps to register data resulting from the data acquisition. To facilitate this, the following acquisition protocol may be employed. This protocol presumes that a vessel segment has been selected for angiography and intravascular ultrasound. First, the angiogram is made and the resulting digital image series is sent to a processing unit. It is noted that the angiogram may consist of a series of images acquired sequentially to obtain images corresponding to different phases of the cardiac (ECG) cycle. Second, the IVUS catheter is advanced over a guide wire. The guide wire has markers with known marker distance (for example, the markers are 1 centimeter apart). The IVUS catheter is placed at the starting position of the pullback. Third, an X-Ray image series is acquired while the IVUS catheter is in the starting position and the C-arm is in the same position as during the angiogram acquisition of the first step; the digital image data is sent to the processing unit. Fourth, continuous IVUS pullback with known pullback speed is performed and the IVUS data is sent to the processing unit. The IVUS data acquisition may be started at the same time as the pullback. Alternatively, the start of the pullback may be marked in the IVUS data. Fifth, software on the processing unit is used to register the IVUS data with the X-Ray angiogram. Sixth, the user can scroll through the IVUS frames and can see in the angiogram where the images were taken. Seventh, the intervention continues.

In an embodiment, the registration of the IVUS data with the x-ray angiogram (referred to in the fifth step of the protocol above) is performed as follows. The acquired data comprises an angiographic image series, an additional x-ray image series (showing the markers and/or probe), and a series of intravascularly acquired data (e.g., a series of IVUS images). These data need to be registered. One step of the registration involves registering the angiographic image series with the additional x-ray image series. The purpose of this step is to combine images corresponding to the same phase of the cardiac cycle. If ECG data is available for the two image series, then this data can be used, as appreciated by a person skilled in the art. Image-based techniques to select pairs of images corresponding to the same phase of the cardiac cycle are known to the skilled person and not explained herein. Briefly these techniques use the fact that the markers in the additional series should coincide with a vessel filled with contrast agent in the angiographic series. This registration of the angiographic series with the additional x-ray series in principle only maps the corresponding frame numbers. Optionally a slight transformation is applied to compensate for e.g. respiratory motion (using vessel and guide wire information: the guide wire should coincide with the vessel).

Another step of the registration involves calculating the starting position and acquisition trajectory of the probe. This step involves detecting the probe and/or markers in at least one image of the additional x-ray image series. By detecting the probe, a reference position (in this case the starting position) of the probe is established. By detecting the markers, the trajectory that is traversed by the probe during the intravascular acquisition as seen in the x-ray image is established. By themselves, the positions of the markers only indicate individual points on the trajectory. However, by means of known curve fitting techniques a continuous trajectory is established. These curve fitting techniques may be improved by using the information in the angiographic image registered to the additional x-ray image, because the trajectory coincides with a vessel in that angiographic image. The angiographic image may thus be used to establish the order in which the markers are traversed by the probe and/or to refine the trajectory in between the markers. Another step of the registration involves calculating the number of intravascularly acquired data samples (for example the number of IVUS images) acquired while the probe is traversing from one marker to the next marker. This number of data samples can be calculated from the speed with which the probe traverses (for example the IVUS pullback speed) and the distance between successive markers on the wire/catheter.

Another step of the registration involves associating an angiogram of the angiographic series with an intravascularly acquired data sample (e.g. IVUS image). This is based on the ECG data that is recorded along with the image and data acquisitions. This step is repeated for all relevant intravascularly acquired data samples.

Another step of the registration involves establishing a point on the associated angiogram corresponding to the position of the probe at the time of acquiring the data sample. The number of data samples acquired between the moment on which the probe starts to move and the moment the data sample under consideration is acquired, is used in combination with the computed number of intravascularly acquired data samples while the probe is traversing from one marker to the next marker, to obtain the position along the catheter/wire where the data sample was acquired. Using the trajectory in between the markers as established by means of curve fitting, the position on the angiogram corresponding to the probe position is established.

In an embodiment, the X-Ray sequence of the starting position of the IVUS probe as well as IVUS imaging are ECG-triggered to improve quality of the registration.

The protocol set forth may be used by interventional cardiologists who acquire IVUS data in a patient. The method can be used for any clinical application where intravascular imaging is performed with a pull back of an imaging catheter and needs to be registered with 2D projection data.

Although in this description the emphasis is on acquiring IVUS images and localization of IVUS images in a corresponding angiogram, the method readily extends to other modalities. Instead of or in addition to IVUS, other intravascular modalities may be used, such as optical coherence tomography, thermography, spectroscopy, chemography, and intravascular MRI. IVUS and other acquired data may be processed to obtain for example virtual histology, elastography, or palpography images.

Figure 4:
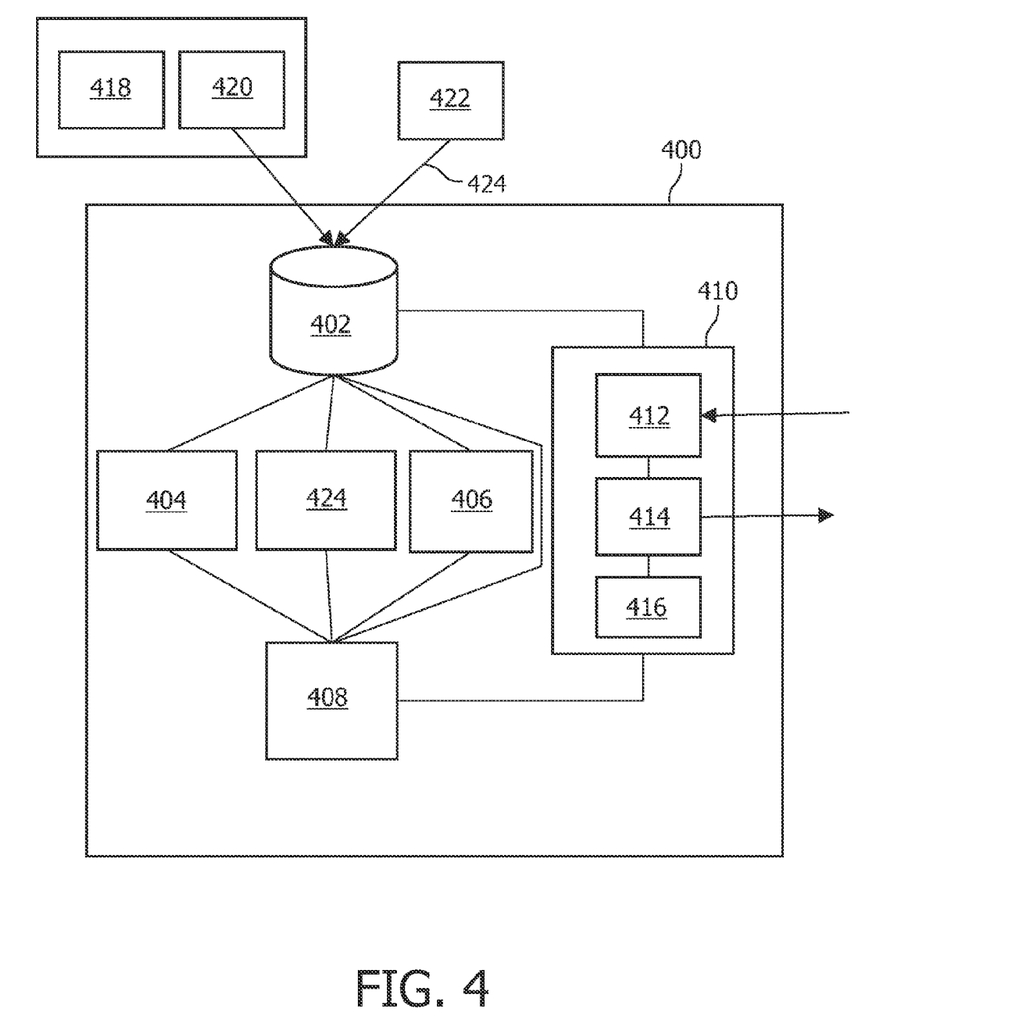
FIG. 4 illustrates an embodiment.

FIG. 4 is a diagram illustrating some aspects of the invention. It shows a system 400, for example an image processing workstation, for mapping data obtained by an intravascular probe to an x-ray image. It is provided for estimating a position in an x-ray projection image 202 corresponding to a projected probe position of an intravascular probe 422 at a time of acquiring data from the intravascular probe 422 via input 424. The data acquired from the intravascular probe is stored in storage medium 402. The intravascular probe is for example an IVUS probe, an optical coherence tomography (OCT) probe, an intravascular thermometer, or an intravascular MRI probe. These and other intravascular probes are known in the art. The x-ray image is provided by an x-ray system 100 comprising an x-ray generator 418 and an x-ray detector 420. The patient is located in between the x-ray generator and the x-ray detector to obtain an x-ray image of the interior of the patient. Such x-ray systems are known in the art, for example the Philips Allura FD10 (produced by Philips Medical Systems) is used. The image data is stored in storage medium 402. Storage medium 402 can be any kind of volatile or non-volatile memory as known in the art. Image data stored can include a series of at least one x-ray image containing a marker wire or a catheter with markers introduced in a vessel, for example a human artery, particularly a coronary artery. It can also include a series of at least one angiogram taken from the same perspective as the x-ray image series. It will be appreciated that an angiogram can be a particular type of x-ray image. Marker wires are known in the art. Also, a series of at least one data sample acquired with the intravascular probe is stored. ECG data corresponding to the images and data samples is also stored if available. Storage medium 402 also stores auxiliary information such as predetermined distances of a plurality of markers 302 on the marker wire, and a distance along the acquisition trajectory of the intravascular probe relative to at least one of the markers. This latter distance refers to the position of the probe at the time of acquiring the data relative to the position of the marker at the time of acquiring the x-ray image.

At least one x-ray image is fed to a marker detector 404. This marker detector identifies in the x-ray image a plurality of markers 302 positioned at the predetermined relative positions along an acquisition trajectory of the intravascular probe. Marker detectors are known in the art, for example from Lindeberg and Egmont-Petersen referenced above.

Interpolator 408 establishes a position in the x-ray image corresponding to a position of the intravascular probe at a time of acquiring the data in dependence on the distance along the acquisition trajectory between the intravascular probe and at least one of the markers. Interpolators are known in the art. For example, a linear interpolator or a spline interpolator can be used. The distance between the probe and the marker is sufficient to know where the probe is relative to the markers. For example the interpolator first establishes two successive markers, where the probe position is in between the two successive markers. It can do this because the distances between the markers are known. Then, the exact position in the x-ray image is established by interpolating the projected acquisition trajectory in between the two successive markers using for example linear or spline interpolation.

Module 406 establishes the distance along the acquisition trajectory between the intravascular probe and at least one of the markers in dependence on a predetermined relative probe reference position and a portion of the acquisition trajectory traversed by the probe in between the probe reference position and the intravascular probe. The reference position may be a probe starting position, the acquisition trajectory may be a probe pullback trajectory, and the portion of the acquisition trajectory may be a length of the probe pullback trajectory from the probe starting position to the position of the probe at the time of acquiring the data. The module 406 may be arranged for determining the length of the probe pullback trajectory from the probe starting position to the position of the probe at the time of acquiring the data in dependence on a pullback speed and a pullback duration.

An alternative way to establish the distance along the acquisition trajectory between the intravascular probe at the time of acquiring the data and at least one of the markers is based on the length of the portion of the marker wire that is inserted in the human body and the length of the portion of the probe catheter that is inserted in the human body. Since the positions of the markers on the wire and the position of the probe on the catheter can be measured before inserting them into the patient, and both the wire and the probe follow the same trajectory through the vessel lumen, this provides sufficient information to establish the distance between the probe and at least one of the markers.

Typically, if the x-ray acquisition is performed directly before the probe acquisitions, the probe may be visible in the x-ray acquisition at a starting position of a pullback trajectory. In that case, a probe detector 424 is used for identifying in the x-ray image the intravascular probe 422. This may be based on the same algorithms used in marker detector 404. Additionally, ridge detection and template matching may be used as will be appreciated by a skilled person. The interpolator 408 uses the found position of the intravascular ultrasound probe in the x-ray image. This is especially useful if the distance along the acquisition trajectory to the first encountered marker position is known, to establish the probe positions along this first portion of the acquisition trajectory.

A user interaction module 410 comprises a user input 412 such as a keyboard and mouse or a dedicated input device for enabling a user to select the data for viewing. The user can select an x-ray image; in response, the system will show that x-ray image along with the intravascularly acquired data corresponding to the ECG phase of the x-ray image, and mark the positions in the x-ray image corresponding to the shown intravascularly acquired data (for example by means of numeric indicators). Alternatively, the user selects a data sample; in response, the module 410 shows that data sample along with the x-ray image corresponding to the ECG phase of the data sample, and mark therein the position of the intravascular acquisition. To that end, a display 414 and indicator 416 are provided. Indicator 416 may also indicate in the x-ray image an orientation of the probe at the time of acquiring the data in dependence on a direction of the acquisition trajectory at the relevant position. For example, indicator 416 comprises computer instructions for rendering computer graphics objects such as arrows to point to the position of the probe in the x-ray image. Such computer instructions for example include calls to OpenGL library routines known in the art.

In an embodiment, the system 400 is integrated in an x-ray imaging apparatus 100, for example the above-mentioned Philips Allura FD10. The x-ray equipment comprises an x-ray generator and an x-ray detector for obtaining at least one x-ray image, an input for receiving data obtained by an intravascular probe (for example a network connection or using DICOM compliant interconnectivity as known in the art), a marker detector for identifying in the x-ray image a plurality of markers positioned at predetermined relative positions along an acquisition trajectory of the intravascular probe, and means for establishing a position in the x-ray image corresponding to a position of the intravascular probe at a time of acquiring the data in dependence on the identified markers, the predetermined relative positions, and a predetermined position of the intravascular probe relative to at least one of the identified markers.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. The carrier may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for estimating within a 2D space a position in an x-ray projection image corresponding to a projected position of an intravascular probe in a vascular system at a time of acquiring data from the intravascular probe, the system comprising:
   an x-ray detector configured to, acquire a 2D x-ray projection image; and
   a processor coupled to a memory wherein the memory configures the processor to
   identify in the 2D x-ray projection image utilizing the 2D space, a projected position of a plurality of markers located at predetermined distances along a trajectory of the intravascular probe, and
   interpolate within the 2D space the projected position of the intravascular probe on the trajectory corresponding to a location within the 2D x-ray projection image of the intravascular probe at a time of acquiring the data which is a different time then when the 2D x-ray projection image is acquired, dependent on a distance along the trajectory between the intravascular probe at the time of acquiring the data and at least one of the markers along the trajectory.

2. The system according to claim 1, further comprising an image detector configured to acquire angiographic projection images having a same orientation with respect to a patient as the 2D x-ray projection image, the processor is further configured to indicate on the angiographic projection image the interpolated position of the intravascular probe.

3. The system according to claim 2, wherein the positions of the markers are interpolated along a projected vascular system visible in the angiographic projection image.

4. The system according to claim 1, wherein the processor is further configured to calculate within the 2D space the distance along the trajectory between the intravascular probe and at least one of the markers based on a reference position and a distance along the trajectory traversed by the intravascular probe between the reference position and the location of the intravascular probe at the time of acquiring the data.

5. The system according to claim 4, wherein the reference position is a starting position, the trajectory is a trajectory of pullback of the intravascular probe, and the distance is a length along the trajectory from the starting position to the position of the intravascular probe at the time of acquiring the data.

6. The system according to claim 5, wherein the processor is further configured to determine the length based on speed and duration of the pullback.

7. The system according to claim 1, wherein the intravascular probe is an intravascular ultrasound probe.

8. The system according to claim 3, wherein the processor is further configured to identify the intravascular probe in the 2D x-ray projection image, wherein the interpolation is based on a first position of the intravascular probe in the 2D x-ray projection image and a distance traversed by the intravascular probe between the first position and a second position of the intravascular probe at the time of acquiring the data.

9. The system according to claim 1, wherein the processor further comprising at least one input peripheral and the processor is configured to receive input from the at least one input peripheral specifying a location on the x-ray projection image to be displayed.

10. The system according to claim 2, wherein the processor is further configured to indicate an orientation of the intravascular probe at the time of acquiring the data based on a direction of the trajectory at the position of the intravascular probe at the time of acquiring the data.

11. An x-ray imaging apparatus for estimating within a 2D space a position in an x-ray projection image corresponding to a projected position of an intravascular probe in a vascular system at a time of acquiring data from the intravascular probe, the apparatus comprising:
    an x-ray detector configured to acquire a 2D x-ray projection image of a plurality of markers located at predetermined distances along a trajectory of the intravascular probe;
    a processor coupled to a memory wherein the memory configures the processor to acquire angiogram projection images and configures the processor to, within the 2D space, interpolate in the 2D x-ray projection image the projected position corresponding to the position within the 2D x-ray projection image of the intravascular probe on the trajectory at the time of acquiring data which is a different time then when the 2D x-ray projection image is acquired, dependent on a distance along the trajectory between the intravascular probe at the time of acquiring the data and at least one of the plurality of markers in the 2D x-ray projection image.

12. A method of estimating within a 2D space a position in an x-ray projection image corresponding to a projected position of an intravascular probe in a vascular system at a time of acquiring data from the intravascular probe, the method comprising acts of:
    acquiring a 2D x-ray projection image of a plurality of markers located at known marker distances along a trajectory of the intravascular probe;
    pulling the intravascular probe over the trajectory;

acquiring the data while the intravascular probe is pulled over the trajectory;

interpolating within the 2D space in the 2D x-ray projection image a projected position within the 2D x-ray projection image of the intravascular probe on the trajectory at the time of acquiring the data which is a different time then when the 2D x-ray projection image is acquired, dependent on a distance along the trajectory between the intravascular probe at the time of acquiring the data and at least one of the plurality of markers along the trajectory.

* * * * *